United States Patent [19]

Ingwersen

[11] Patent Number: 5,638,419
[45] Date of Patent: Jun. 10, 1997

[54] SPIRAL-HELICAL SCAN COMPUTED TOMOGRAPHY APPARATUS

[75] Inventor: Hartwig Ingwersen, Uttenreuth, Germany

[73] Assignee: Siemens Aktiengesellschaft, Munich, Germany

[21] Appl. No.: 583,621

[22] Filed: Jan. 5, 1996

[30] Foreign Application Priority Data

Feb. 16, 1995 [DE] Germany ............ 195 05 276.5

[51] Int. Cl.⁶ .................................................. H05G 1/00
[52] U.S. Cl. .............................. 378/4; 378/195; 378/208
[58] Field of Search .......................... 378/4, 193–198, 378/208

[56] References Cited

U.S. PATENT DOCUMENTS 5,109,397  4/1992  Gordon et al. .................. 378/4
5,448,607  9/1995  McKenna ....................... 378/195

FOREIGN PATENT DOCUMENTS 7730503    3/1979  Germany.
9218322.0  1/1994  Germany.

*Primary Examiner*—Don Wong
*Attorney, Agent, or Firm*—Hill, Steadman & Simpson

[57] ABSTRACT

A computed tomography apparatus permits tomographic exposures to be produced using a single gantry, but with a number of differently located patient tables. For this purpose, the gantry is mounted so as to be movable on a horizontal surface, so that it can be moved from a standby position into a number of differently-located operating positions. The gantry has a connector mechanism permitting temporary and releasable attachment of the gantry to the patient support table with which it is being used at a given time. The connector mechanism can be controlled by the computed used to generate the tomographic images for finely positioning the gantry relative to the patient table.

3 Claims, 2 Drawing Sheets

SPIRAL-HELICAL SCAN COMPUTED TOMOGRAPHY APPARATUS

BACKGROUND OF THE INVENTION

1. Field of the Invention

The present invention is directed to a computed tomography apparatus, and in particular to a computed tomography apparatus of the type for conducting a spiral-helical scan.

2. Description of the Prior Art

Standard computed tomography systems include a housing, referred to as a gantry, which has support elements therein supporting a measuring unit, also known as a scan frame, which includes an x-ray radiator and a radiation detector. The scan frame is rotatable around an examination region so that a subject disposed in the examination region is trans-irradiated by x-rays from the x-ray radiator from a number of successive angular directions (projections). The subject lies on a patient table, in the examination region. From the output signals generated by the detector during a scan, a computer generates an image of a slice of the examination region (i.e. a slice of the patient), which is displayed on a monitor.

In medicine, minimally invasive surgical interventions for diagnosis and therapy are being increasingly conducted with CT (computed tomography) monitoring. So-called spiral helical scan computed tomography is frequently employed for this purpose which, in addition to the above-described operation, employs a longitudinal displacement of the patient table with the patient thereon, so that an image of a larger volume of the subject can be obtained. Spiral-helical CT has thus made a step from simple slice imaging to volume imaging, and therefore it is possible, instead of making a slice exposure for monitoring the position of a surgical instrument, to make three-dimensional exposures (volume exposures) for reliable positioning of surgical instruments in a critical region of the subject. The anatomotical details in this critical region may vary from patient to patient, thus making such volume imaging particularly useful for such interventional purposes.

German Utility Model 92 18 322 discloses an apparatus for invasive therapy employing computed tomography monitoring, with the computed tomography apparatus being adjustable relative to a patient bed along a longitudinal direction. This known system can be employed only in combination with one patient bed, i.e., a patient bed that is specifically configured to interrelate with the other components of the computed tomography system. German Utility Model 77 30 503 discloses a mobile x-ray apparatus which is provided for producing x-ray exposures at the hospital bed of a patient. The production of computed tomograms with this mobile apparatus is not possible.

SUMMARY OF THE INVENTION

It is an object of the present invention to provide a computed tomography apparatus wherein the production of slice or volume exposures is possible in combination with a number of differently located patient support tables.

This object is achieved in accordance with the principles of the present invention in a computed tomography apparatus having a gantry which is mounted so as to be movable from a standby position into a number of different operating positions, and having a connector mechanism with permits the gantry to be temporarily (releasably) attached or docked to any of a number of patient tables respectively disposed at different locations.

In the computed tomography apparatus of the invention, the gantry can be moved from the standby position, which may be remote from a treatment or examination location, to the location at which a particular patient support table which is to be used is located. The production of computed tomography exposures is thus possible in combination with a number of different patient support tables, but with only one gantry. The gantry together with the scan frame contained therein can also be employed in several operating rooms, by moving the gantry from room to room. For introduction into a particular operating position, the gantry is firmly docked or attached to the patient table in use at the time. Fine positioning relative to the body region which is desired to be examined, as well as adjusting the longitudinal displacement motion to a desired speed required for producing a particular volume exposure, ensues using a mechanism which allows the entire gantry to be movable on wheels or rails, so that the gantry can be precisely moved and positioned in the desired manner. This mechanism may be an electromechanical device having at least one threaded rod drive and positioned sensors for monitoring the displacement resulting from rotation of the threaded rod inside a threaded collar. In another embodiment, the mechanism may be in the form of a hydraulic drive.

DESCRIPTION OF THE PREFERRED EMBODIMENTS

Figure 1:
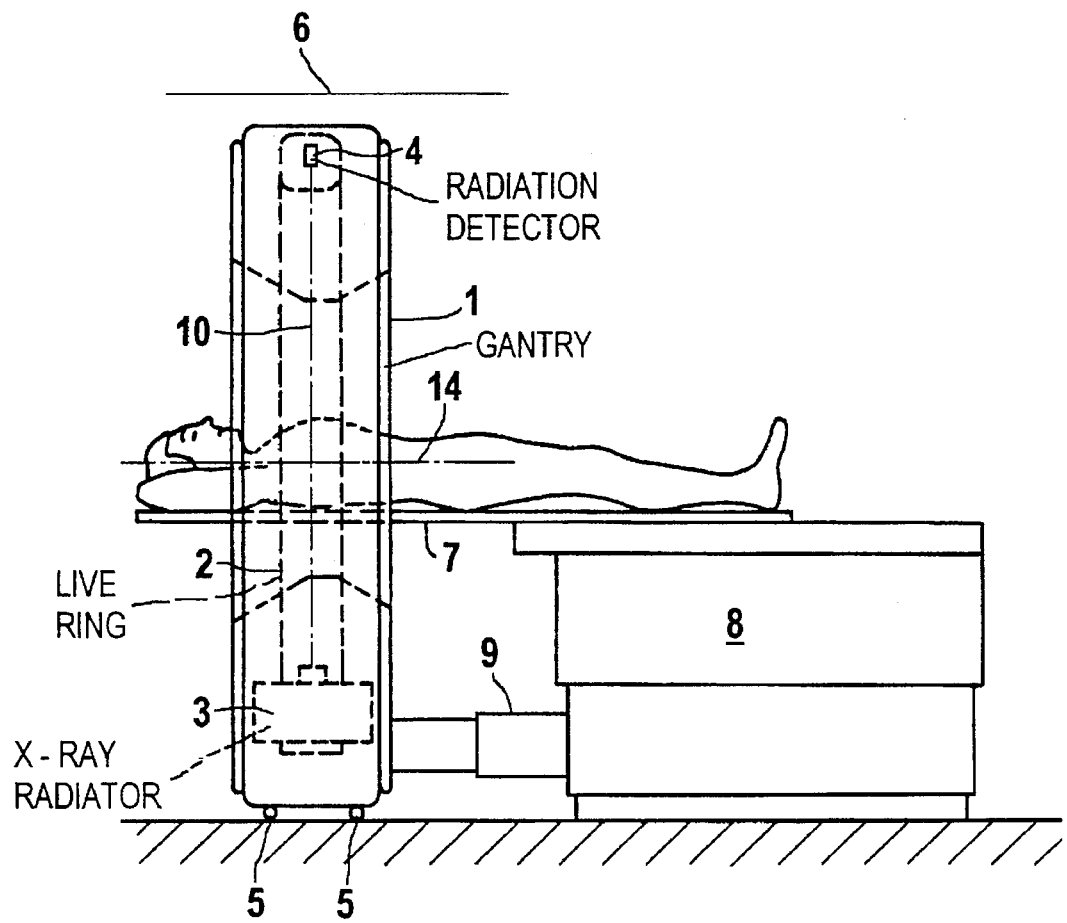
FIG. 1 is a side view of a computed tomography apparatus constructed in accordance with the principles of the present invention.

The computed tomography apparatus shown in FIG. 1 has a gantry 1 containing a live ring 2 on which an x-ray radiator 2 and an arcuate radiation detector 4 are mounted. The gantry 1 is movable on a horizontal surface in the direction of the double arrow 6, by means of rollers 5, or by means of rails mounted on the horizontal surface. A patient to be examined lies on a patient table 7.

Figure 3:
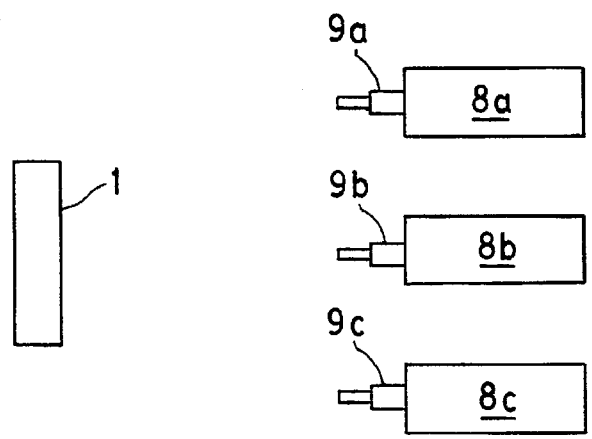
FIG. 3 schematically illustrates the use of a single gantry with multiple patient tables in accordance with the invention.

For producing computed tomography exposures, the gantry 1 is moved from a standby position (not shown) to a location surrounding the patient table 7, and is docked to a stationary base 8, on which the patient table 7 is movably mounted, by means of a connector mechanism 9. The connector mechanism 9 may, for example, be telescoping, and permits a fine positioning of the gantry 1 in the direction of the double arrow 6. This makes the gantry 1 suitable for producing computed tomography exposures in combination with a number of patient tables, disposed at respectively different locations as shown in FIG. 3 wherein the gantry 1 can be coupled to any of patient tables bases 8a, 8b and 8c, respectively having connector mechanisms 9a, 9b and 9c. For helical-spiral CT exposures (volume exposures), the connector mechanism 9 can be coordinated with the computer-controlled operation of the remainder of the apparatus so that it shifts the gantry 1 in one of the directions of the double arrow 6 during rotation of the live ring 2, with the x-ray radiator and radiation detector 4 mounted thereon, around a system axis 14.

Figure 2:
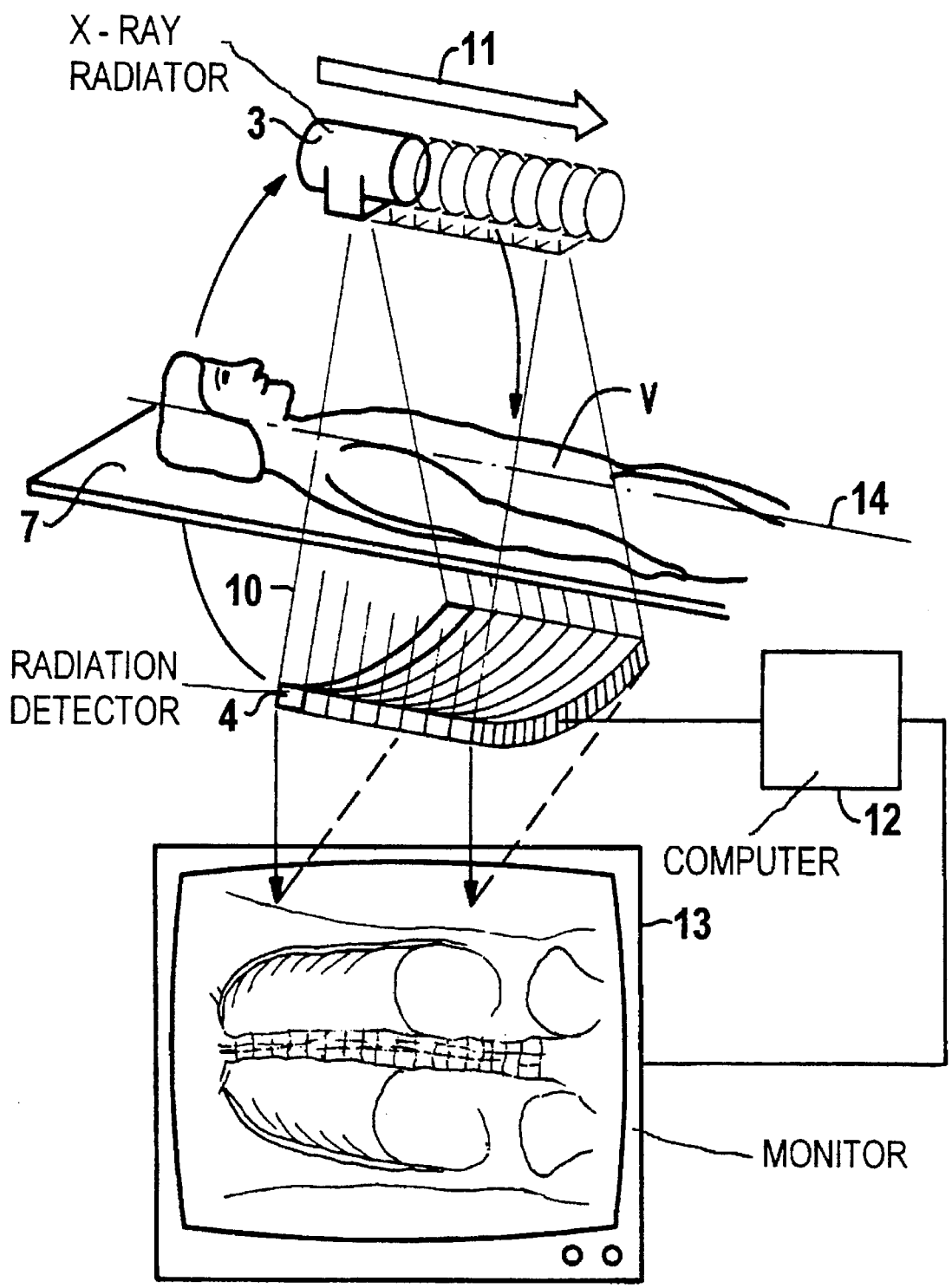
FIG. 2 is a schematic illustration showing the operation of the computed tomography apparatus of FIG. 1 for conducting a spiral-helical scan.

The production of spiral-helical CT exposures is described in more detail in combination with FIG. 2. As shown in FIG. 2, the x-ray radiator 3 emits a fan-shaped x-ray beam 10, which penetrates the examination subject and is incident, in attenuated form, on the radiation detector 4. The radiation detector 4 is composed of a row of individual detector elements, curved around the focus of the x-ray radiator 3. For scanning a volume of the patient, the gantry 1 and the live ring 2 with the x-ray source 2 and the radiation detector 4 mounted thereon, are displaced by a predetermined distance in the direction of the arrow 11, i.e. in the right direction of the double arrow 6 in FIG. 1, while the x-ray radiator 3 and the radiation detector 4 are rotated around the system axis 14. The data corresponding to incident x-rays, generated by the individual detector elements of the radiation detector 4, are supplied to a computer 12 which calculates images of the patient therefrom in a known manner, for example a three-dimensional image of the scanned volume V. These images are displayed on a viewing monitor 13.

The connector mechanism 9 can be formed by a parallel guide having a number of rods sliding in respective sleeves, with one or more position sensors being provided to generate feedback signals indicating the current position of a selected element or elements of the connector mechanism 9. The displacing movement in the directions of the arrow 6 can be produced by a threaded rod which is rotated inside a rigidly-mounted threaded collar, or by a hydraulic drive.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computed tomography apparatus for use on a horizontal surface, comprising:

a gantry containing a scan frame mounted for rotation around a system axis, and an x-ray radiator and a radiation detector mounted on said scan frame for conducting a scan by trans-irradiating an examination region from a plurality of angular directions with said radiation detector generating image data at each angular direction, said examination region extending through said gantry and being surrounded by said scan frame;

a patient table adapted for supporting an examination subject in said examination region;

means for movably mounting said gantry on said horizontal surface for permitting said gantry to be moved from a standby position, remote from said patient table, into a plurality of different operating positions; and connector means for temporarily and releasably connecting said gantry to said patient table in a selected operating position and for, during said scan, displacing said gantry along said system axis; and computer means, supplied with said image data, for producing an image of said examination subject from said image data; and display means for displaying said image.

2. A computed tomography apparatus as claimed in claim 1 wherein said connector means comprises means for finely positioning said gantry relative to said patient table.

3. A computed tomography apparatus for use on a horizontal surface, comprising:

a gantry containing a rotatably mounted scan frame and an x-ray radiator and a radiation detector mounted on said scan frame for trans-irradiating an examination region from a plurality of angular directions, said radiation detector generating image data at each direction, said examination region extending through said gantry and being surrounded by said scan frame;

a plurality of patient tables, each adapted for supporting an examination subject in said examination region;

means for movably mounting said gantry on said horizontal surface for permitting said gantry to be moved from a standby position, remote from said patient table, into a plurality of different operating positions; and each of said patient tables having connector means for temporarily and releasably connecting said gantry to that patient table for selected use with said gantry for trans-irradiating said examination region; and computer means, supplied with said image data, for producing an image of said examination subject from said image data; and display means for displaying said image.

* * * * *